United States Patent [19]

Kalender et al.

[11] Patent Number: 4,651,335
[45] Date of Patent: Mar. 17, 1987

[54] PATIENT SUPPORT BODIES INCLUDING REFERENCE ELEMENTS FOR A TOMOGRAPHIC APPARATUS

[75] Inventors: Willi Kalender, Kleinseebach; Guenter Schmitt; Christoph Suess, both of Erlangen, all of Fed. Rep. of Germany

[73] Assignee: Siemens Aktiengesellschaft, Berlin and Munich, Fed. Rep. of Germany

[21] Appl. No.: 698,852

[22] Filed: Feb. 6, 1985

[30] Foreign Application Priority Data

Apr. 12, 1984 [DE] Fed. Rep. of Germany ... 8411550[U]

[51] Int. Cl.[4] ............................................. G01N 23/00
[52] U.S. Cl. ................................. 378/20; 378/208; 378/163; 378/177; 378/195; 378/207
[58] Field of Search ............... 378/20, 208, 195, 177, 378/163, 164, 207; 5/434, 436

[56] References Cited

U.S. PATENT DOCUMENTS

| | | | |
|---|---|---|---|
| 3,417,413 | 12/1968 | Gage | 5/434 |
| 3,897,777 | 8/1975 | Morrison | 378/208 |
| 4,053,781 | 10/1977 | Hounsfield | 378/20 |
| 4,181,858 | 1/1980 | Moore | 250/445 |
| 4,233,507 | 11/1980 | Volz . | |
| 4,319,136 | 3/1982 | Jinkins | 378/163 |
| 4,333,637 | 6/1982 | Shelton | 269/322 |

FOREIGN PATENT DOCUMENTS

| | | | |
|---|---|---|---|
| 2432525 | 2/1975 | Fed. Rep. of Germany | 378/208 |
| 0155790 | 12/1979 | Japan | 378/20 |

OTHER PUBLICATIONS

"Precise Measurement of Vertebral Mineral Content Using Computed Tomography" Cann et al., Journal of Computer Assisted Tomography, 1980, pp. 493–500.

*Primary Examiner*—Craig E. Church
*Assistant Examiner*—John C. Freeman

[57] ABSTRACT

Patient support elements, such as pillows, are disposed on opposite sides of an examination subject lying on a supporting bed in a tomographic apparatus. The patient support bodies include one or more reference elements having known composition and characteristics which are reproduced in the image at a display unit. Standardization of the measured values is thereby achieved in a manner which is independent of the apparatus itself.

3 Claims, 2 Drawing Figures

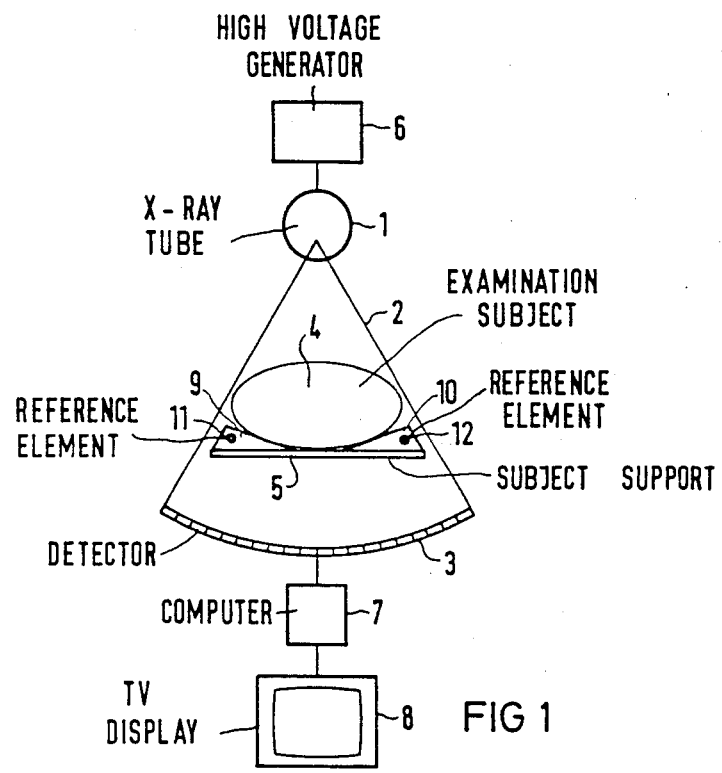
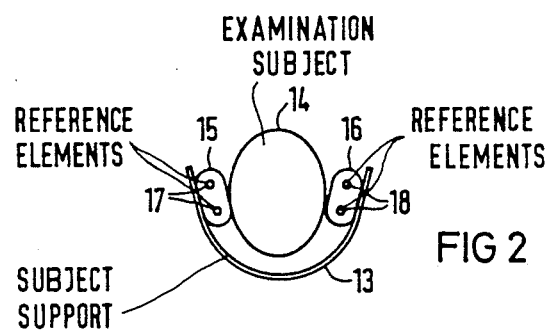

PATIENT SUPPORT BODIES INCLUDING REFERENCE ELEMENTS FOR A TOMOGRAPHIC APPARATUS

BACKGROUND OF THE INVENTION

1. Field of the Invention

The present invention relates to diagnostic devices for generating tomographic images of an exposure subject, and in particular to patient support bodies containing reference elements therein for use in such a device.

2. Description of the Prior Art

The use of reference elements in the generation of computer tomographics is known, the reference elements being comprised of a known composition and having known attenuation values. When scanning an examination subject to produce a computer tomograph, the reference bodies are automatically scanned at the same time and reproduced in the cross-sectional image. A reference measurement utilizing reference bodies positioned close to the patient's body is therefore achieved without burdening the patient. The reference bodies appear in the image in every event, i.e. independent of the particular transversal layer being investigated. The reference bodies enable an automatic self-compensation of the computer tomography system for every measurement, independent of variable system parameters such as beam quality and drift. The reference bodies further enable a quantitative evaluation of transversal layer images and quantitative comparisons of transversal layer images recorded at different computer tomograph installations. The images of the reference bodies in the transversal layer image are not superimposed on the image of the patient.

Patient support units are known in the art wherein the reference bodies are inserted in the housing aperture of the bed which receives the patient, this apparatus having two patient beds disposed at both sides of the housing. The two-bed apparatus, with a gap therebetween, is outdated and modern support systems now comprise only one bed which extends through the housing aperture of the apparatus. Arrangement of the reference bodies in this manner is therefore no longer possible. In modern patient support systems, it is known to rigidly attach the reference bodies in the inside of the bed. This results in a relatively expensive structure for the bed and moreover it is not possible to individually select the reference bodies which are to be used for a particular scan, that is, it is not possible to undertake replacement of reference bodies or to remove them as needed.

Another reference body arrangement is described in "Precise Measurement Of Vertebral Mineral Content Using Computed Tomography", Cann et al., Journal Of Computer Assisted Tomography, 1980, at pages 493–500. This unit is a plexiglass member which is matched in form to that of the bed surface, and which has a plurality of bores filled with different solutions. This plexiglass member is placed on the bed surface and the patient is seated thereon. This system has the disadvantages of the size of the unit, the difficulty of comfortably placing the patient thereon, and of the relatively high beam attenuation which is achieved by the unit. Moreover, this arrangement is well-suited only for examinations of the trunk region.

Lastly, it is also known to secure reference bodies to a belt which is placed around the patient. This technique, however, is also relatively involved.

SUMMARY OF THE INVENTION

It is an object of the present invention to provide a means for placing reference bodies near a patient in a tomographic apparatus which involves minimal structural outlay and minimum discomfort to the patient.

The above object is inventively achieved in a tomographic apparatus having a plurality of patient support members, such as pillows, placed on either side of the patient as the patient lies on the tomographic apparatus bed. The pillows may be comprised of, for example, cellular material which can be provided in a simple manner with openings into which the reference bodies can be introduced. The pillows may be placed, for example, near the patient's head. An easy interchange of the reference bodies is also possible.

DESCRIPTION OF THE DRAWINGS

FIG. 1 is a schematic block diagram of a tomographic apparatus constructed in accordance with the principles of the present invention.

FIG. 2 is a further embodiment of a patient support system for use in the apparatus shown in FIG. 1 constructed in accordance with the principles of the present invention.

DESCRIPTION OF THE PREFERRED EMBODIMENTS

The tomographic installation shown in FIG. 1 has a high voltage generator 6 which feeds an x-ray tube 1 for generating a fan-shaped x-ray beam 2. The x-ray beam 2 irradiates an examination subject 4 lying a patient support or bed 5. Radiation passing through the examination subject 4 is incident on a radiation receiver 3, which may consist of, for example, 512 individual detectors. For scanning a selected transversal slice of the patient 4, the x-ray tube 1 and the receiver 3 are rotated through 360° around the examination subject 4. The high voltage generator 6 may feed the x-ray tube 1 so as to produce pulsed or constant radiation, so that sets of data are generated at pre-determined angular positions. The sets of data are supplied from the radiation receiver 3 to a computer 7 which calculates the attenuation coefficients of pre-determined picture elements from the generated data sets and visually reproduces the images at a TV display 8.

Two wedge-shaped patient support members 10 and 11, such as pillows comprised of cellular material, are disposed on either side of the examination subject 4, for providing additional support for the examination subject 4 in addition to the patient bed 5. Each of the pillows 9 and 10 have openings therein which receive reference elements 11 and 12, which may be interchanged in the openings in the pillows 9 and 10. The reference elements 11 and 12 have known attenuation coefficients and are accordingly reproduced in the picture on the TV display 8. A standardization of the attenuation values which is independent of the tomography apparatus is thus achieved.

In a further embodiment shown in FIG. 2, the subject support consists of a curved support 13 for receiving the head 14 of a examination subject. In this embodiment, two pillows 15 and 16 comprised of cellular material are disposed between the patient's head 14 and the support 13. Each of the pillows 15 and 16 in this embodiment includes two reference elements 17 and 18 which, as the embodiment shown in FIG. 1, may be interchanged with other reference elements as needed.

Either of the bearing pillows 9 and 10 or 15 and 16 may be provided with one or more reference bodies. The supporting pillows 9, 10, 15 and 16 are preferably disposed symmetrically on opposite side of the examination subject 4, as shown in FIGS. 1 and 2. The reference elements 11, 12, 17 and 18 may consist of solid material, but may also consist of tubes filled with fluid having known attenuation values.

The invention has heretofore been described in combination with a computer tomograph apparatus, but is also suitable for use in other diagnostic devices such as, for example, nuclear magnetic resonance devices. Given the above-described manner of arranging the pillows 9 and 10 (or 15 and 16) a relatively problem-free application of the reference elements is possible in all body regions. The same wedges as shown in FIG. 1 can be employed in the cranial, neck, trunk and extremity regions. Fastening of the wedges to the patient is not necessary because the material comprises the wedges adapts closely to the shape of the body and will not dislocated. The reference elements 12 and 11 (and 18 and 17) produce only a slight additional beam attenuation and accordingly have a low negative effect on the image quality. The patient support bodies can be employed in any apparatus with auxiliary measurements. Adaptation to the curvature of the patient's support bed or the like is eliminated. Inserts comprising the reference elements can be easily interchanged and inserts comprised of different materials or different material concentrations can be easily substituted.

Interpretation of the reference element dimensions and correction of the picture values in the transversal slice image are undertaken fundamentally in the same fashion as other known systems making use of reference elements. This is a matter of software programming, and does not form a part of the present invention.

Although modifications and changes may be suggested by those skilled in the art it is the intention of the inventors to embody within the patent warranted hereon all changes and modifications as reasonably and properly come within the scope of their contribution to the art.

We claim as our invention:

1. In a diagnostic apparatus for generating slice images of an examination subject having a subject-supporting bed, means for generating an x-radiation field in which said subject is disposed, a means for generating measured signals dependent on the material distribution of the examination subject based on attenuation of said x-radiation by said subject, and a computer for calculating picture element information of the examination subject slice from said measured signals, the improvement of:

a plurality of patient support pillows disposed beneath said examination subject on said bed, said pillows being comprised of a material adapting to the shape of said examination subject, each pillow having at least one reference element therein, said reference element consisting of material having a known composition and x-radiation attenuation for use in monitoring the level of said x-radiation.

2. The improvement of claim 1 wherein said pillows are comprised of cellular material.

3. The improvement of claim 1 wherein said pillows are disposed symmetrically about said examination subject.

* * * * *